United States Patent [19]

John, Jr.

[11] 4,218,920
[45] Aug. 26, 1980

[54] NUCLEAR FUEL PARTICLE BULK DENSITY DETERMINATION

[75] Inventor: Clarence D. John, Jr., Verona, Pa.

[73] Assignee: Westinghouse Electric Corp., Pittsburgh, Pa.

[21] Appl. No.: 9,560

[22] Filed: Feb. 5, 1979

[51] Int. Cl.² .............................................. G01N 9/02
[52] U.S. Cl. .................................. 73/422; 73/422 TC
[58] Field of Search .................... 73/433, 435, 422 TC

[56] References Cited

U.S. PATENT DOCUMENTS

| | | | |
|---|---|---|---|
| 1,966,712 | 7/1934 | Fisher et al. | 73/422 TC |
| 2,687,037 | 8/1954 | Saxe | 73/433 |
| 3,221,152 | 11/1965 | Jones | 73/433 |
| 3,726,143 | 4/1973 | Enarsson | 73/422 TC |
| 3,949,614 | 4/1976 | Abonnene | 73/422 TC |

*Primary Examiner*—S. Clement Swisher
*Attorney, Agent, or Firm*—Edward L. Levine; Z. L. Dermer

[57] ABSTRACT

Systems for, within a sealed environment, determining the bulk density of radioactive nuclear fuel particles flowing in a process stream. A carrier having a known weight and a channel of known volume is selectively shuttled between the flowing particles and a weigh cell. Thus, from the weight of a known volumetric sample, the bulk density is determined. The carrier and selected portions of the cell and carrier transporter are enclosed within a sealed structure to contain the radioactive material within a controlled environment. Subsequent to density determination, the particle sample is dumped, preferably back into the flowing stream, by structure which rotates the carrier or opens a door at the bottom of the channel. The systems also provide for sealing of the housing at various positions of the carrier.

7 Claims, 11 Drawing Figures

NUCLEAR FUEL PARTICLE BULK DENSITY DETERMINATION

BACKGROUND OF THE INVENTION

1. Field of the Invention

This invention relates to nuclear fuel particles, and more particularly provides sealed systems for determining the bulk density of the particles flowing in a processing stream.

2. Description of the Prior Art

During the fabrication of many types of nuclear fuel, the fuel is in a particulate form. Because of radiation considerations, it is desirable that the particles be contained within a controlled, sealed environment. The fabrication process accordingly involves transport of the particles within sealed conduits.

In order to ensure the high degree of quality necessary for fabricated nuclear fuel, many parameters must be determined at various stages of the fabrication procedure, including, where fuel particles are involved, a determination of the particle bulk density. It is therefore desirable to provide remotely operable sampling systems which accurately determine the fuel particle bulk density while maintaining the flowing particles and the sample within a controlled environment.

SUMMARY OF THE INVENTION

This invention provides systems which, within a sealed environment, remotely determine the bulk density of radioactive fuel particles flowing in a generally downward stream within a conduit or housing. The systems each include a carrier or shuttle of known weight which has a channel of known volume. The channel is inserted into the flowing particle stream, the known volume filled, and the carrier or the portion of the carrier containing the channel is weighed. Thus, the bulk density of a fuel particle sample, the mass per unit volume, can be readily determined. Selected components, such as the carrier and portions of the weigh cell and carrier transport mechanism, are contained within a sealed enclosure including the conduit and its housing. Subsequent to density determination, the carrier is transported back to the flowing stream or to a separate hopper where the sample is dumped.

In one embodiment the carrier is a horizontally-disposed cylinder having a channel cut in its side. The carrier is transported by a remotely demountable coupling, such as an electromagnet, and is matingly sized to an opening in the flowing particle housing so that insertion of the carrier seals the housing. The housing is provided with structure, such as a spring-loaded piston or door, which seals the housing upon removal of the carrier. The housing also is provided with a mechanism which rotates the carrier to dump the sample.

In another embodiment the carrier includes a dump door which opens at the bottom to dump the sample. The door can be actuated by a remotely demountable transport arm or by structure contained within the housing.

In another embodiment a portion of the carrier is always sealed to the housing, although the carrier reciprocatingly translates and also rotates. The carrier is preferably cylindrical, having an opening completely through its side and a pan matingly sized to the opening. Subsequent to filling, the pan is positioned so that it can be removed from the carrier by structure cooperating with a weigh cell. Preferably, the cell of an extension thereon moves upwardly through the opening and lifts the pan. The pan is provided with a lateral extension at its upper surface, also contoured to the cylindrical carrier shape, which seats the pan within the opening. The extension also slides across suitably configured structure within the housing so that upon rotation of the carrier and contained pan to dump the sample, the pan is maintained within the carrier opening.

BRIEF DESCRIPTION OF THE DRAWINGS

The advantages, nature and additional features of the invention will become more apparent from the following description, taken in connection with the accompanying drawings, in which.

DESCRIPTION OF THE PREFERRED EMBODIMENTS

Figure 1:
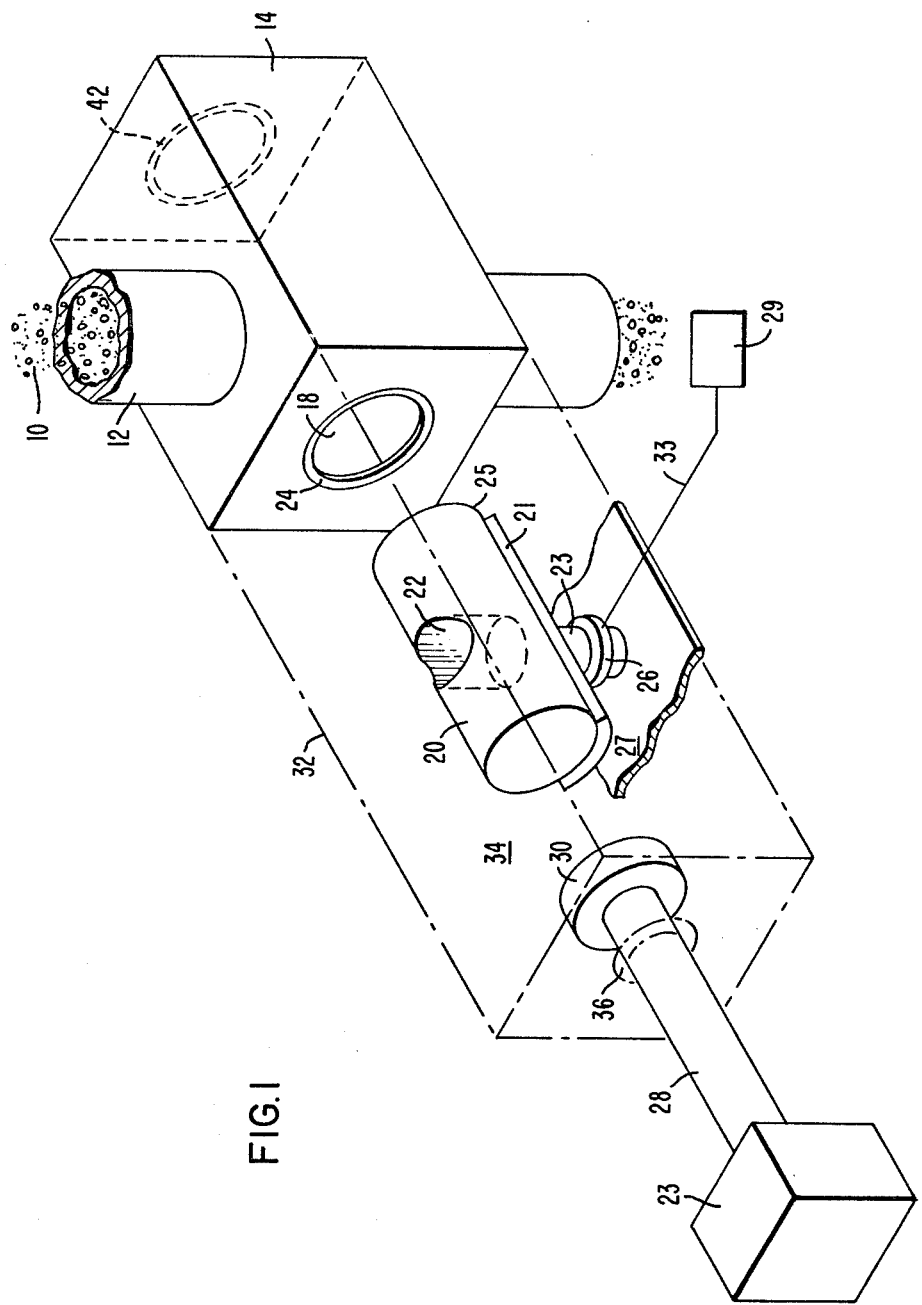
FIG. 1 is a perspective view of one embodiment of the invention.

Referring now to FIG. 1, there is shown a nuclear fuel particle bulk density determination system. Radioactive fuel particles 10, such as oxides or carbides of uranium, thorium or plutonium, flow in a downward direction within a conduit 12. Sealed to the bottom of the conduit is a housing 14 through which the particles 10 typically pass to another conduit 16, also sealed to the housing.

The housing contains an aperture 18 sized to allow passage of a carrier 20 into and out of the housing 14 and the flowing particle 10 stream. The carrier 20 is of predetermined weight, cylindrical, and has a channel 22, the channel 22 being of predetermined volume and open at one end. The carrier 20 and housing aperture 18 are preferably compatibly sized so that when any portion of the carrier 20 is within the housing 14, the flowing fuel particles 10 are sealed within the housing. A separate seal 24 can be disposed within the aperture for this purpose. The seal 24 or aperture 18 also function to remove excess fuel particles as the carrier 20 is withdrawn from the housing, thereby ensuring a known volume of particles.

Figure 2:
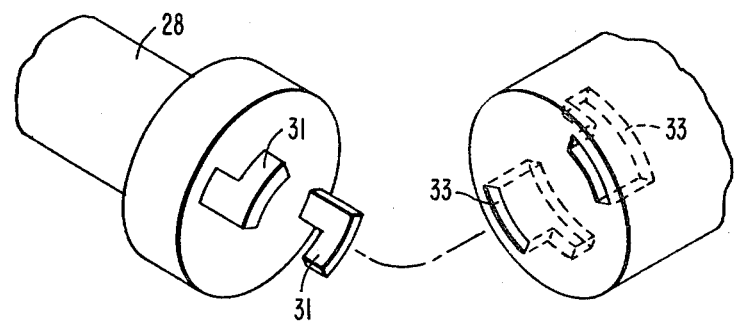
FIG. 2 is a perspective view of an alternate attachment configuration.

Compatibly configured to support the carrier 20 is a tray 21 affixed to a shaft 23 cooperatively associated with a weigh cell 26. The cell 26 is supported by a portion 27 of a sealed enclosure 32, and cooperates with a readout device 29 disposed externally of the enclosure 32. In operation, the carrier 20 is transported between a position which allows a weight determination by the cell 26 and a position where the channel 22 is aligned with the flowing particle 10 stream within the housing. The carrier 20 is transported by an arm 28 which is demountably attached to the carrier. This can be accomplished, for example, by an electromagnet 30 or, as shown in FIG. 2, a mechanical attachment which engages a generally L-shaped extension 31 on the arm 28 with a receiving semi-covered aperture 33 in the end of the carrier when rotated in one direction, and which disengages upon rotation in the opposite direction.

Selected portions of the system components are sealingly encased within the enclosure 32. This provides a contained, hermetically-sealed environment 34 for the fuel particles. As shown, the enclosure 32 is preferably affixed to the housing 14, and contains a sealed aperture 36 which allows reciprocating motion of the arm 28. The only additional penetration of the enclosure 32 need be to allow for passage of an electrical lead 33 between the weigh cell 26 and the readout device 29. Alternatively, the readout device can be disposed within the enclosure 32 in a position such that a visual indicator can be seen through a window (not shown) in the enclosure 32. It will be noted that utilization of a weigh cell 26 as opposed to a weigh scale provides for a smaller enclosure.

In operation, the arm 28 is actuated and attached to the carrier 20. The arm 28 is then moved laterally, transporting the carrier from the tray 21 to the housing 14. The tray 21 is preferably positioned close to the housing to minimize the distance of carrier travel and the size of the enclosure 32. The leading edge 25 of the carrier 20 or the aperture 18 can be beveled to assure proper entry of the carrier into the housing 14. The carrier is positioned by the arm 28 with its channel 22 facing into the flowing fuel particle 10 stream, thereby filling the channel 22. The carrier 20 is then withdrawn by the arm 28, to the cooperating position with the tray 21 and cell 26, and the arm 28 disconnected. It will be noted that during withdrawal, excess particles above the known channel 22 volume are knocked away by the sealed aperture 18, 24. The carrier and contained particles are then weighed by the cell 26 and the density determined based upon the particle weight in the known volume. The tare weight of the shaft 23, tray 21 and carrier 20 are properly accounted for. Calculational and recording means, well known to those skilled in the art, can be used and remotely disposed for this purpose. The sample is then returned to the housing by reconnecting the arm 28 to the carrier 20. Once within the housing 14, the carrier 20 is rotated approximately 180 degrees to dump the particle sample back into the flowing stream. The carrier can continue rotation another 180 degrees back to its "fill" position, for retrieval of another sample, or can be withdrawn. It will be noted that the sample can be dumped in a separate bin or hopper (not shown) outside of the housing 14 if desired. It can also be dumped into another conduit (not shown) disposed parallel to conduit 16 which extends from the bottom of the housing 14. It will also be apparent that the carrier can be partially withdrawn from the housing so that its end portion is maintained within the housing aperture 18 until another sample is desired, so as to seal the housing. The carrier can be rotated by the arm 28 and its drive mechanism 23 or by other structure 42 such as shown in FIGS. 3 and 4.

Figure 3:
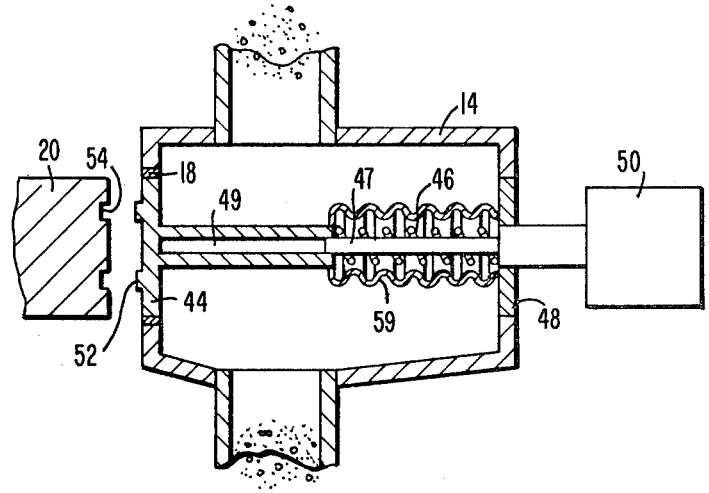
FIGS. 3 and 4 are section views, in elevation, of alternative sealing and rotation arrangements.

FIG. 3 shows an arrangement including a piston 44 and associated spring 46 which cooperate to seal the housing aperture 18 when the carrier is removed. The carrier 20, being pushed by the arm, compresses the spring 46 upon entry into the housing. The spring surrounds a shaft 47 having, for example, a square cross-section, connected to a rotating wheel 48 sealed to the housing. The shaft 47 slidingly engages the mating opening 49. The wheel 48 is driven by a rotating drive 50 to rotate the shaft 47, piston 44 and carrier 20 which engages the piston through structure such as mating extensions 52 and receivers 54. It will be noted from FIG. 3 that the housing is preferably slanted or funneled at the bottom to avoid buildup of particles. Collapsible bellows 59 can be utilized about the spring 46 to avoid a buildup of fuel particles.

Figure 4:
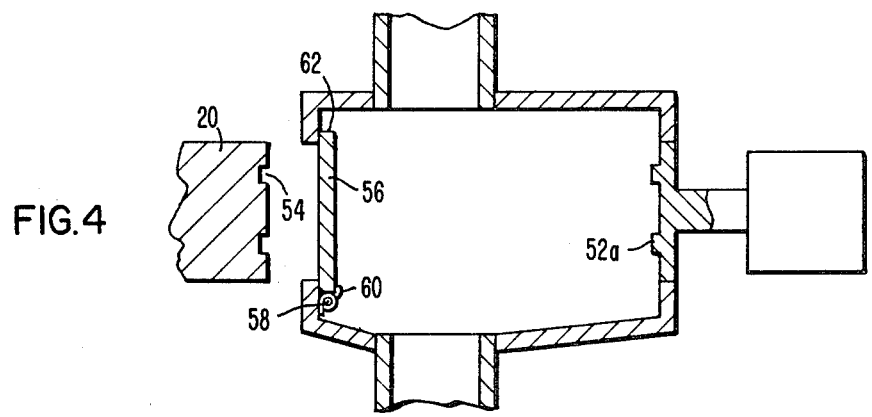
Figure 5:
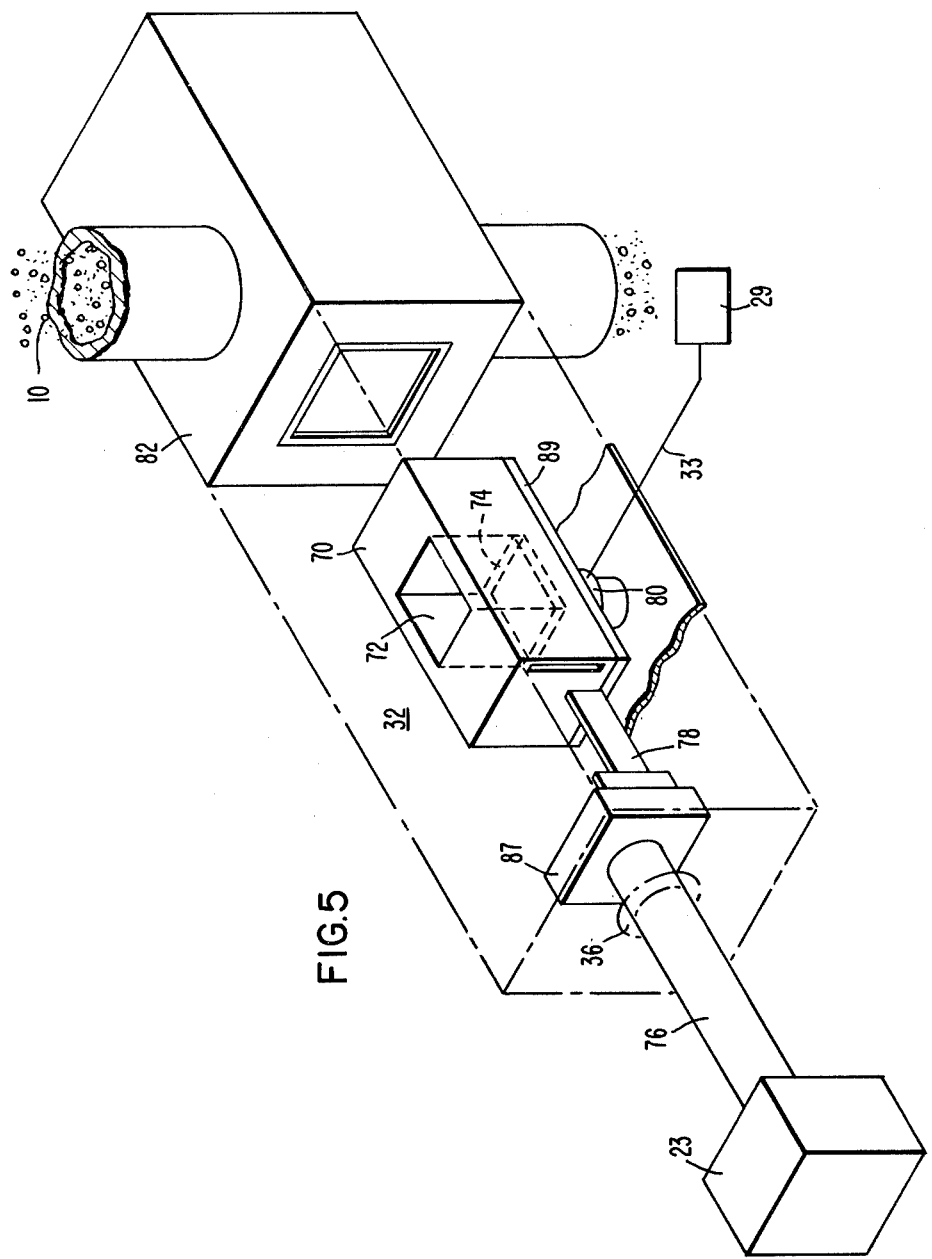
FIG. 5 is a perspective view of another embodiment of the invention.

FIG. 4 shows another sealing system including a door 56 on a pivot 58. Upon contact of the carrier 20 with the door 56, the door opens and is closed upon removal of the carrier by the spring 60. The carrier is preferably withdrawn with the open end of the channel 22 opposite the pivot to avoid interference between the end 62 of the door 56 and the channel 22. Rotation within the housing is accomplished through interaction of extensions 52a and receivers 54.

Figure 6:
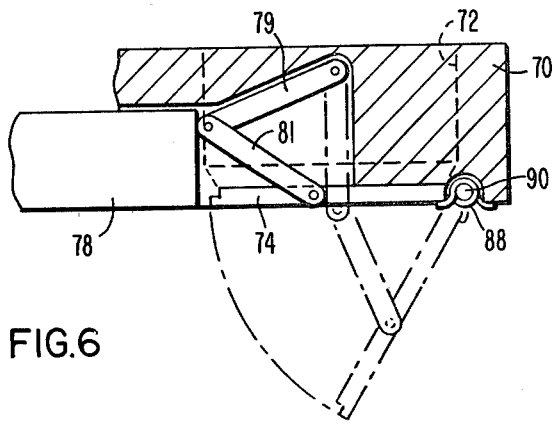
FIG. 6 is a section view, in elevation, of a carrier and dump mechanism in accordance with the embodiment of FIG. 5.
Figure 7:
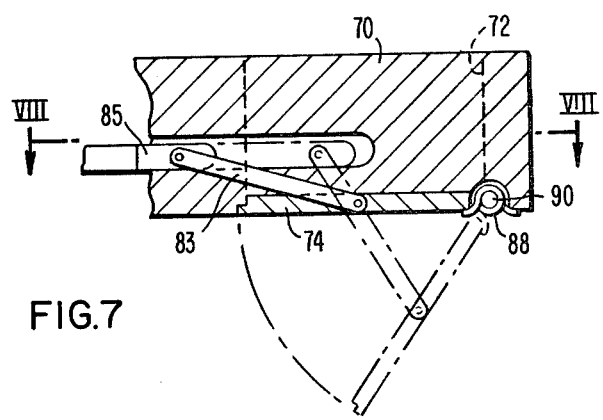
FIG. 7 is an elevation view, in section, of another dump mechanism.
Figure 8:
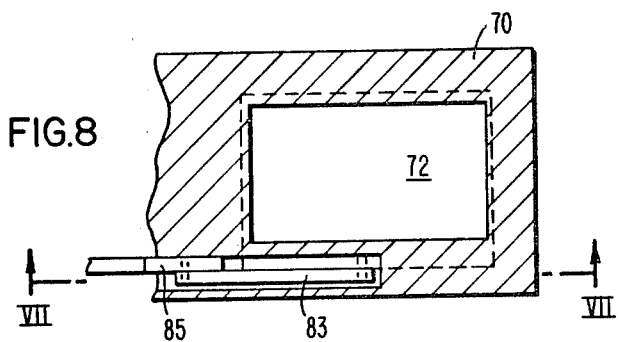
FIG. 8 is a plan view section taken at VIII—VIII of FIG. 7.

Another embodiment system is shown in FIGS. 5 through 8. Here a carrier 70 is provided with a channel 72 which is open at its upper end and which contains a dump door 74 at the bottom. Instead of rotating the carrier to dump the particles 10, the door 74 opens to carry out the discharge when actuated by the arm 76 and an arm extension 78 or structure similar to extension 78 disposed within the housing, but which acts at the opposite end of the carrier 70. As the arm extension 78 is extended, the carrier 70 is moved into a stop position within the housing and the extension 78 then forces rods 79, 81 into an extended position to open door 74, as shown in FIG. 6, or forces a slider 85 and pinned rod 83 to translate to place the door 74 in the open position as shown in FIG. 7. The door is preferably biased to the closed position, such as by spring 88 associated with pivot 90. Alternatively, actuation can be provided by structure similar to extension 78 but oriented in the opposite direction and disposed within the housing which forces open the door as connector 87 (FIG. 5) pushes the carrier 70 and rods against the structure. In either case, the force required by extension 78 to open the door only becomes sufficient upon the carrier reaching a preselected stop position within the housing.

The system operation is similar to that described above, the arm 76 transporting the carrier 70 between a weigh cell 80 and tray 89 and a housing 82. The carrier can remain at rest within the particle stream and with the dump door open to allow free flow of the stream.

The enclosure 32 hermetically seals the system, being penetrated only by arm 76 through seal 36 and the sealed electrical lead 33. Alternatively, the entire arm 76 and drive mechanism 23 can also be disposed within the enclosure 32, requiring only actuation leads to penetrate the enclosure through sealed penetrations. This orientation however, requires a much larger enclosure volume than the preferred compact configuration shown and does not allow direct access to the drive mechanism for maintenance.

Figure 9:
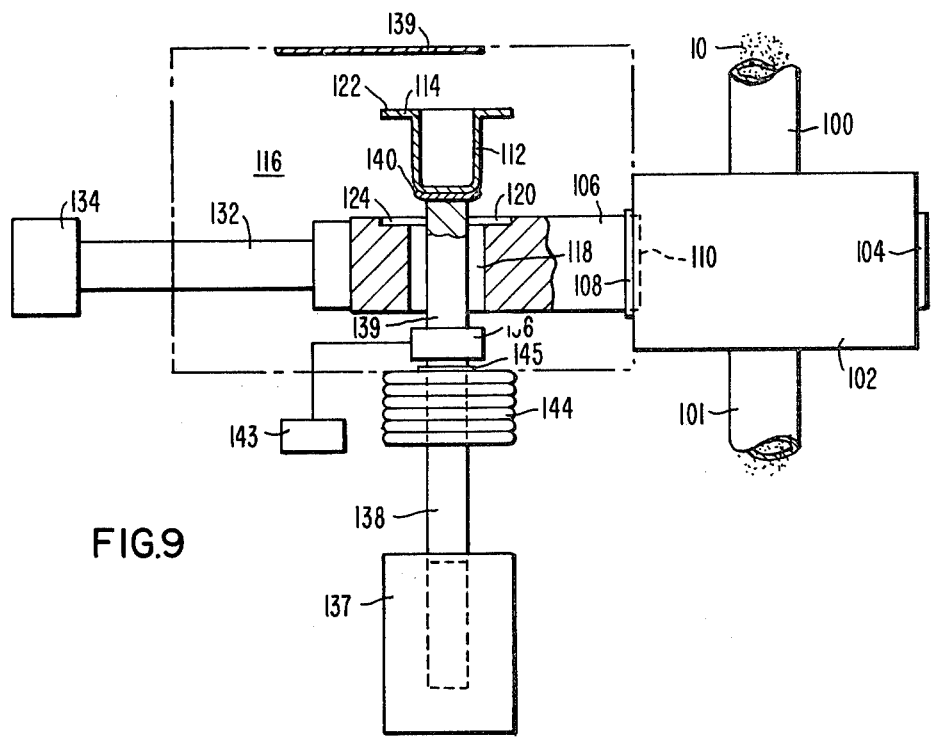
FIG. 9 is an elevation view, partially in section, of another embodiment of the invention.
Figure 10:
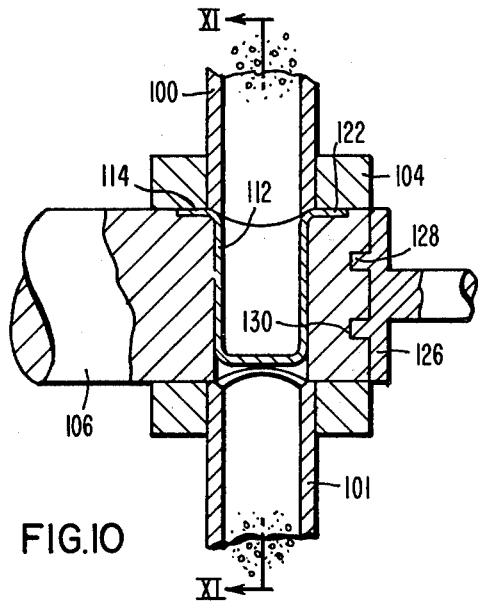
FIG. 10 is a section view, in elevation, of a carrier positioned within the housing of FIG. 9.
Figure 11:
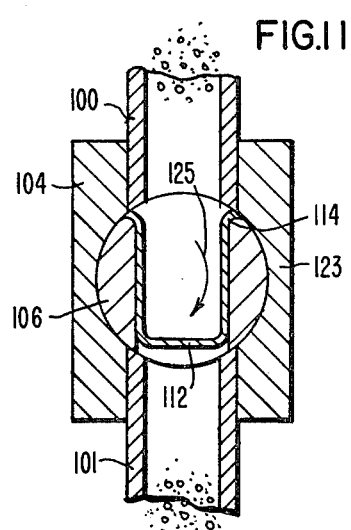
FIG. 11 is a section view taken at XI—XI of FIG. 10.

Another embodiment is shown in FIGS. 9 through 11. Fuel particles 10 flowing through conduit 100 enter housing 102 which can include an extension or sealed chamber 104, and are discharged through conduit 101. A carrier 106 of circular cross section is matingly configured to a seal 108 in housing aperture 110, and a portion of the carrier is maintained within the housing 102 at all times to seal the housing. The carrier 106 includes a removable pan 112 matingly sized to fit within the carrier. The pan, as with all of the components, in all embodiments, within the sealed environment 116, is comprised of a material substantially immune to attack by the fuel particles, such as stainless steel, and the pan further includes a non-stick lining, such as DuPont Teflon. The pan includes a lip 114 about its upper periphery, generally contoured to the circular cross section of the carrier 106. The carrier has a channel 118 therethrough and a cut 120 to receive the lip 114. Ears 122 can also be provided on the lip 114, with a mating extension 124 of the cut 120, to assist in properly seating the pan and in maintaining the pan in position during rotation, as hereafter described.

As illustrated best in FIGS. 10 and 11, the lip 114 and/or ears 122 of the pan 112 are larger than the cross section of the conduits 100, 101, so that the carrier, including the pan, can be rotated without the pan being removed from its seated position. Rotation of the carrier, including the pan, to dump a sample, can be accomplished in a variety of manners, including a rotating member 126 in the sealed chamber 104 having extensions 128 which mate with receivers 130 of the carrier. Alternatively, as shown in FIG. 9, the carrier 106 can be actuated by a fixedly mounted arm 132 which, through an actuator 134 preferably positioned outside of the sealed environment 116, extends, retracts and rotates the carrier 106.

Also disposed within the sealed environment 116 is a weigh cell 136. The cell is movable by a shaft 138, and atop the cell is an arm 139 with a top 140 sized and configured to match the bottom of the pan 112 and to freely pass through the channel 118. The shaft 138 is retractable into drive unit 137. The top 140 can also include means to grip or attach to the pan, such as a magnetic connection to a magnetically influenced material of construction or insert for the pan 112. The sealed environment 116 about the cell 136 can be defined by a hermetic seal about the shaft 138 and additionally, as shown, can include a bellows 144, which extends and retracts upon movement of the shaft 138. The weight detected by the weigh cell 136 is not influenced by interaction of the shaft 138 and the bellows. The sealed environment 116 accordingly is bound by the structures 139 affixed to the housing and the collapsible bellows 114 sealingly affixed to the shaft 138. For additional sealing redundancy, the structure 139 can also contain a seal 145 about the shaft 138. It will be noted that any frictional affects of the seal or bellows upon the shaft do not effect weight determination as would be the case if a weigh scale were utilized.

During operation, the carrier 106 is fully inserted by the actuator 134 into the housing 102 until the pan 112 is aligned with the flowing fuel particles and filled. The carrier is then withdrawn to a position aligning the top 140 with the aperture 118 and the pan. The shaft 138, cell 136 and arm 139 are then extended upwardly, removing the pan from the carrier, and the weight noted by a remote readout device 143. The pan is then reseated in the aperture as the shaft 138 is retracted. The system remains in this position until another sample is desired. Then, the carrier is fully inserted into the housing and rotated 180 degrees to dump the previous sample, and further rotated another 180 degrees to align the open end of the pan with the flowing particles. The filled pan and carrier are then withdrawn for another cycle. The end portion of the carrier toward the housing is always maintained within the housing to act as a seal. A sample can be taken at the next desired interval by fully reinserting the pan into alignment with the flowing particles and performing the necessary rotation.

It will be apparent that the systems disclosed, particularly that of FIG. 9, can be readily adapted to removal of stationary fuel particles in a large storage container. Since numerous other changes may be made in the above described systems without departing from the spirit and scope thereof, it is intended that all matter contained in the foregoing description be interpreted as illustrative and not in a limiting sense.

I claim:
1. Apparatus for determining the bulk density of radioactive nuclear fuel particles flowing downwardly through a housing, comprising:
 a carrier having a portion of known weight, said portion having a channel of known volume;
 a cell for weighing said portion and the contents of said channel;
 means for transporting said carrier between said weigh cell and housing, said means reciprocatingly moving said device between a first position wherein said channel is exposed to said flowing particles within said housing and a second position wherein said portion is in a cooperative position with said weigh cell;
 means for selectively dumping said particles contained within said channel; and
 structure for enclosing said carrier and portions of said weighing device and transport means within a sealed environment, said structure cooperatively sealing said housing such that said fuel particles are contained within said sealed environment and housing at all times.

2. Apparatus for determining the bulk density of radioactive nuclear fuel particles flowing downwardly through a housing, comprising:
 a carrier of known weight having therein a channel of known volume;
 a cell for weighing said carrier and the contents of said channel;
 means for transporting said carrier between said weigh cell and into said housing, said means being remotely demountable from said carrier upon placement of said carrier into a cooperating position with said weigh cell, said transporting means further being capable of inserting said carrier into said housing such that said channel is positioned with its open end upward and thereby is filled with said flowing particles;
 means for rotating said carrier so as to position said channel with its open end down so as to dump said particles; and
 means for sealingly enclosing said carrier and portions of said weigh cell and transport means to said housing whereby said carrier is sealingly enclosed while in cooperation with said weighing device, in transport between said device and housing, and while within said housing.

3. Apparatus of claim 2 wherein said carrier is insertable into said housing through an opening cooperatively configured to said carrier such that said carrier is insertable into said housing through said opening so as to seal said housing.

4. Apparatus of claim 2 wherein said housing includes an opening for passage of said carrier and further comprises means for sealing said opening upon removal of said carrier from said housing.

5. Apparatus for remotely and sealingly determining the bulk density of radioactive nuclear fuel particles flowing downwardly through a housing comprising:
   a carrier of known weight having a channel of known volume disposed with its open end upward, the bottom of said channel being openable and biased into a closed position;
   a cell weighing said carrier and the contents of said channel;
   means for transporting said carrier between said weigh cell and into said housing, said means being remotely demountable from said carrier upon placement of said carrier into a cooperating position with said weigh cell;
   means for selectively opening said channel bottom; and
   means for sealingly enclosing said carrier and portions of said weigh cell and transport means to said housing, whereby said carrier is sealingly enclosed at all times.

6. Apparatus for remotely and sealingly determining the bulk density of radioactive nuclear fuel particles flowing downwardly through a conduit comprising:
   a housing sealingly enclosing the bottom of said conduit, said housing having a discharge at the bottom;
   a pan of known volume having a lateral extension at the top;
   a carrier having an opening therethrough sized to receive said pan, said pan being held in place in said carrier when in an upright position by said lateral extension, a portion of said carrier being contained within and sealed to said housing at all times, said portion being reciprocatingly movable within said housing;
   a reciprocatingly movable cell for weighing said pan;
   means for inserting and withdrawing said opening of said carrier and said pan into said flowing particles within said housing and for rotating said carrier and pan within said housing, said pan being maintained in position in said carrier upon rotation by said lateral extension contacting retaining structure within said housing, said insertion, withdrawal and rotating means aligning said pan with said weighing device upon removal of said opening from said housing such that said weighing device moves said pan from a seated position within said carrier; and
   structure for sealingly enclosing said carrier, pan and cell, said structure being sealed to said housing.

7. Apparatus of claim 6 wherein said cell is movable by a reciprocating shaft and wherein said sealing structure comprises a collapsible bellow sealed to said shaft.

* * * * *